United States Patent [19]

Grosskinsky et al.

[11] 4,227,021

[45] Oct. 7, 1980

[54] PRODUCTION OF ADIPIC ACID FROM ACIDIC WASH WATERS

[75] Inventors: Otto-Alfred Grosskinsky, Ludwigshafen; Norbert Petri, Frankenthal; Johannes Hein, Weinheim; Hans Leitner, Frankenthal, all of Fed. Rep. of Germany

[73] Assignee: BASF Aktiengesellschaft, Fed. Rep. of Germany

[21] Appl. No.: 901,235

[22] Filed: Apr. 28, 1978

[30] Foreign Application Priority Data

May 14, 1977 [DE] Fed. Rep. of Germany ... 2721858

[51] Int. Cl.$^2$ .................. C07C 51/24; C07C 55/14
[52] U.S. Cl. ................... 562/513; 562/524; 562/525; 562/529; 562/593
[58] Field of Search .......... 260/531 R, 537 P, 527 R; 562/513, 525, 529, 524

[56] References Cited

U.S. PATENT DOCUMENTS

| | | | |
|---|---|---|---|
| 3,365,490 | 1/1968 | Arthur et al. | 260/531 R |
| 3,564,051 | 2/1971 | Haarer et al. | 260/531 R |
| 3,997,601 | 12/1976 | Langley | 260/531 R |

FOREIGN PATENT DOCUMENTS

| | | | |
|---|---|---|---|
| 1921533 | 11/1970 | Fed. Rep. of Germany | 260/531 |
| 1123514 | 8/1968 | United Kingdom | 562/513 |

OTHER PUBLICATIONS

Smeykal et al., Chem. Techn., 13, pp. 132–139 (3–1961).

*Primary Examiner*—Vivian Garner
*Attorney, Agent, or Firm*—Keil & Witherspoon

[57] ABSTRACT

An improved process for producing adipic acid from the acidic wash waters which arise in the process for oxidizing cyclohexane with air, by treatment with nitric acid at from 10° to 50° C., with removal of the heat of reaction by external cooling, wherein the reaction mixture is led, at a flow velocity of at least 2.0 m/sec, as a thin layer spirally in counter-current to the coolant, under conditions which do not perturb the flow of the reaction mixture.

8 Claims, No Drawings

PRODUCTION OF ADIPIC ACID FROM ACIDIC WASH WATERS

The present invention relates to a process for producing adipic acid from the acidic wash waters which arise in the process for oxidizing cyclohexane with air, by treatment with nitric acid at from 10° to 50° C., with removal of the heat of reaction by external cooling.

The oxidation of cyclohexane with air produces, in addition to cyclohexanol and cyclohexanone, acidic wash waters which contain by-products of the reaction ("by-product acid") e.g. monocarboxylic and dicarboxylic acids, esters, lactones, hydroxycarboxylic acids and oxocarboxylic acids of up to 6 carbon atoms. In a conventional process, the by-products dissolved in these acidic wash waters are converted, with or without first removing dissolved cyclohexanol and cyclohexanone by distillation, and after concentrating the solution, into a mixture of dicarboxylic acids by a post-oxidation with nitric acid; this is described, for example, in Chemische Technik, 13 (1961), 137–138. As a rule, this process is carried out at about 50° C. with a residence time of from 1 to 2 hours, and the heat of reaction is removed either by employing cooling surfaces or by distilling off some of the water under reduced pressure at the reaction temperature. To avoid high temperatures and the corrosion which these entail, it is advantageous to remove the heat of reaction, generated by the strongly exothermic reactions, by providing cooling surfaces. However, the effectiveness of such surfaces diminishes substantially within a short time as a result of the deposition of dicarboxylic acids. Hence, the heat of reaction has also been removed by boiling nitrogen dioxide or by a boiling solvent, as disclosed in German Published Application No. 1,277,239. The use of solvents is expensive when the process is carried out industrially, whilst removing the heat by means of boiling nitrogen dioxide is not without its problems.

It is an object of the present invention to remove the heat of reaction through cooling surfaces and to reduce or prevent blockage of the cooling surfaces by deposited dicarboxylic acids, and ensure that the reaction proceeds undisturbed.

We have found that this object is achieved by a process for producing adipic acid from the acidic wash waters which arise in the process for oxidizing cyclohexane with air, by treatment with nitric acid at from 10° to 50° C., with removal of the heat of reaction by external cooling, wherein the reaction mixture is led, at a flow velocity of at least 2.0 m/sec, as a thin layer spirally in counter-current to the coolant under conditions which do not perturb the flow of the reaction mixture.

The novel process has the advantage that it proves possible, by a simple method, to reduce the deposition of dicarboxylic acids on the cooling surfaces to the point that the reaction proceeds undisturbed for long periods.

The process has the further advantage that it is not necessary to use expensive coolants for evaporative cooling.

The acidic wash waters used as starting materials as a rule are obtained with a content of from 20 to 50% by weight of organic substances, which in general comprise from 45 to 55% by weight of ω-hydroxycaproic acid, from 30 to 40% by weight of adipic acid, from 5 to 10% by weight of glutaric acid and succinic acid and from 5 to 15% by weight of monocarboxylic acids. Advantageously, small amounts of dissolved cyclohexanol and cyclohexanone are first removed from the wash waters by azeotropic distillation with water, and the solution is concentrated by evaporation to a strength of from about 30 to 98% by weight.

The oxidizing agent used is nitric acid, the concentration of which is generally from 47 to 78% by weight, especially from 57 to 66% by weight. The concentration of the nitric acid in the reaction mixture is in general from 40 to 50% by weight. Per 100 kg of organic substance contained in the wash waters, from 80 to 100 kg of nitric acid, calculated as anhydrous acid, are required as a rule.

The oxidation is carried out at from 10° to 50° C., advantageously from 10° to 40° C., and especially from 20° to 30° C. In general, the process is carried out under atmospheric pressure but it is also possible to work under superatmospheric pressure or slightly reduced pressure, viz. at from 600 to 1,500 mm Hg. The residence time is in general from 1 to 2 hours and depends both on the concentration of the starting materials in the reaction mixture and on the temperature. The optimum residence time can easily be determined experimentally.

The reaction is strongly exothermic. Hence, efficient cooling is necessary to maintain the desired reaction temperature. According to the invention, the heat of reaction is removed by external cooling, by an arrangement wherein the reaction mixture is led as a thin layer spirally in counter-current to the coolant under conditions which do not perturb the flow of the reaction mixture. The thickness of the layer (i.e. the width of the channel of the heat exchanger used) is as a rule from 6 to 30 mm, advantageously from 10 to 25 mm. Suitable devices are spiral heat exchangers as described, for example, in Grundoperationen Chemischer Verfahrenstechnik (Vauck/Müller), Verlag Th. Steinkopft, Dresden, 1969, pages 392–393. Of course, the reaction mixture is taken from the reaction zone, passed through the spiral heat exchanger and returned to the reaction zone.

It is an essential feature of the invention that whilst being cooled the reaction mixture travels at a flow velocity of at least 2.0 m/sec. Flow velocities of from 2.0 to 7 m/sec., especially 2.5 to 6 m/sec, have proved particularly advantageous. It is a further essential feature of the invention that the flow of the reaction mixture is not perturbed during cooling, i.e., that the flow is unaffected by, for example, internal components of the heat exchanger, such as spacer pins which are conventionally used in spiral heat exchangers. Accordingly, the spiral heat exchangers should not comprise any spacer pins on the side on which the reaction mixture flows. It has proved advantageous to polish the cooling surfaces which come into contact with the reaction mixture.

The spiral heat exchanger is operated in accordance with the conventional industrial methods, for example by leading the material to be cooled outwards on a spiral path or inwards on a spiral path, in each case wth the coolant flowing in the opposite direction.

The reaction mixture is worked up further by, for example, filtering off adipic acid which has crystallized out as a result of cooling. A further quantity of adipic acid can be isolated from the mother liquor, by removing any dissolved nitrogen dioxide by flushing out with, for example, air, removing water by distillation under reduced pressure and then cooling the concentrated mother liquor. It is advantageous to concentrate the mother liquor, with or without first removing the nitrous fumes, so as to bring its nitric acid content to 50-65% by weight and partially to recycle this concentrated solution to the reaction.

Adipic acid produced by the process of the invention may be used, for example, for the manufacture of mixed polyesters or of adipic acid diesters which can be used for the consolidation of soils.

The Examples which follow illustrate the process of the invention.

EXAMPLE 1

Per hour, 2 $m^3$ of 33% strength by weight by-product acid were oxidized with 10 $m^3$ of 60% strength nitric acid in a vessel having a capacity of 20 $m^3$. The heat liberated during the reaction was removed by means of an external spiral heat exchanger (surface area 36 $m^2$). The amount of slurry being circulated was initially 300 $m^3/h$, the heat transfer coefficient k was 1,400 (kcal/$m^2$h.degree), the slurry flow velocity was 3.7 m/sec and the initial temperature was 31° C.

The reaction was stopped when the predetermined final temperature of 40° C. was reached.

The throughput of slurry had fallen to 205 $m^3/h$, the heat transfer coefficient k to 1,050 and the velocity to 2.7 m/sec. The operating time was 257 hours.

EXAMPLE 2

After detaching crusts by heating the solution to 80° C., Example 1 was repeated. The results agreed with those of Example 1.

COMPARATIVE EXAMPLE

Instead of the spiral heat exchanger, a tube-bundle cooler having a surface area of 100 $m^2$ was employed. The reaction was carried out under the same conditions as in Example 1.

After an operating time of only 47 hours, the predetermined final temperature of 40° C. was reached. The throughput of slurry fell from 300 to 250 $m^3/h$, the coefficient k from 1,500 to 320 and the slurry flow velocity from 4.0 to 2.3 /sec.

We claim:

1. In a process for producing adipic acid from the acidic wash waters which arise in the process for oxidizing cyclohexane with air, by treatment with nitric acid at from 10° to 50° C., with removal of the heat of reaction by external cooling, the improvement which comprises leading the reaction mixture at a flow velocity of at least 2.0 m/sec as a thin layer spirally in counter-current to the coolant, under conditions which do not perturb the flow of the reaction mixture.

2. The process of claim 1, wherein acidic wash waters containing from 30 to 98 percent by weight of organic compounds are used as the starting material.

3. The process of claim 1, wherein the temperature is from 10° to 40° C.

4. The process of claim 1, wherein nitric acid of from 47 to 78 percent strength by weight is used.

5. The process of claim 1, wherein from 80 to 100 kg of nitric acid, calculated as anhydrous acid, are used per 100 kg of organic substance contained in the wash waters.

6. The process of claim 1, wherein the flow velocity of the reaction mixture is from 2.5 to 6 m/sec.

7. The process of claim 1, wherein the thickness of the layer is from 6 to 30 mm.

8. The process of claim 1, wherein the thickness of the layer is from 10 to 25 mm.

* * * * *